(12) United States Patent
Krause et al.

(10) Patent No.: US 10,743,892 B2
(45) Date of Patent: Aug. 18, 2020

(54) SURGICAL INSTRUMENTS AND METHODS

(71) Applicant: Stryker European Holdings I, LLC, Kalamazoo, MI (US)

(72) Inventors: Steven Krause, Oakland, NJ (US); Carlos Eduardo Sanchez, Vernon, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 150 days.

(21) Appl. No.: 15/413,746

(22) Filed: Jan. 24, 2017

(65) Prior Publication Data

US 2017/0209154 A1 Jul. 27, 2017

Related U.S. Application Data

(60) Provisional application No. 62/287,648, filed on Jan. 27, 2016.

(51) Int. Cl.
| | | |
|---|---|---|
| *A61B 17/17* | (2006.01) | |
| *A61B 17/16* | (2006.01) | |
| *A61B 17/70* | (2006.01) | |
| *A61B 17/00* | (2006.01) | |
| *A61B 90/00* | (2016.01) | |
| *A61C 1/08* | (2006.01) | |

(52) U.S. Cl.
CPC ...... *A61B 17/1757* (2013.01); *A61B 17/1633* (2013.01); *A61B 17/1671* (2013.01); *A61B 17/7083* (2013.01); *A61B 2017/0023* (2013.01); *A61B 2017/00115* (2013.01); *A61B 2017/00119* (2013.01); *A61B 2090/062* (2016.02); *A61B 2090/0811* (2016.02); *A61C 1/082* (2013.01)

(58) Field of Classification Search
CPC ..................................................... A61B 17/17
See application file for complete search history.

(56) References Cited

U.S. PATENT DOCUMENTS

| | | | | | |
|---|---|---|---|---|---|
| 3,407,424 | A | * | 10/1968 | Lanzarone | .............. A47L 13/24 15/121 |
| 5,571,014 | A | * | 11/1996 | Gregory, Jr. | ......... A61C 8/0089 433/126 |
| 5,662,662 | A | | 9/1997 | Bishop et al. | |
| 6,929,647 | B2 | * | 8/2005 | Cohen | .................. A61B 17/025 606/247 |
| 8,851,201 | B2 | * | 10/2014 | Limberg | ................. F16D 7/044 173/178 |

(Continued)

FOREIGN PATENT DOCUMENTS

| | | |
|---|---|---|
| EP | 1554979 A1 | 7/2005 |
| EP | 2055243 A3 | 5/2009 |

(Continued)

OTHER PUBLICATIONS

Partial European Search Report for EP 17 15 3127 completed Jul. 18, 2017.

*Primary Examiner* — Nicholas W Woodall
(74) *Attorney, Agent, or Firm* — Lerner, David, Littenberg, Krumholz & Mentlik, LLP (57) ABSTRACT

Various surgical instruments and their methods of use are disclosed. The surgical instruments are designed to provide tactile, auditory, and/or visual confirmation to the surgeon that the surgical instrument is being used appropriately and/or fully in accordance with a surgical procedure.

9 Claims, 11 Drawing Sheets

(56) References Cited

U.S. PATENT DOCUMENTS

| | | | |
|---|---|---|---|
| 2006/0179981 A1* | 8/2006 | Cutler | B25B 23/141 81/475 |
| 2011/0313460 A1 | 12/2011 | McLean et al. | |
| 2014/0046336 A1* | 2/2014 | Nino | A61C 1/082 606/96 |
| 2015/0164518 A1* | 6/2015 | Jinton | A61B 17/86 606/96 |
| 2015/0367487 A1* | 12/2015 | Nino | A61B 17/1624 81/473 |
| 2016/0166350 A1* | 6/2016 | Burkhardt | A61B 17/1615 206/572 |

FOREIGN PATENT DOCUMENTS

| | | |
|---|---|---|
| EP | 2853241 A1 | 4/2015 |
| EP | 2962649 A1 | 1/2016 |
| WO | 2014009383 A1 | 1/2014 |

\* cited by examiner

DETAIL B

DETAIL B

SURGICAL INSTRUMENTS AND METHODS

CROSS-REFERENCE TO RELATED APPLICATIONS

This application claims the benefit of the filing date of U.S. Provisional Patent Application No. 62/287,648 filed Jan. 27, 2016, the disclosure of which is hereby incorporated herein by reference.

BACKGROUND OF THE INVENTION

The present invention relates to various surgical instruments and their methods of use.

Some existing drill/depth guides for surgical applications are cumbersome to use. Certain drill/depth guides have mechanisms for altering the drilling depth of the instrument, but frequently such mechanisms are multi-stage or involve cumbersome and inefficient mechanisms. Further, existing drill/depth guides may provide depth-gauge markings for visual indication of the drilling depth, in addition to hard stops in certain cases for preventing further drilling, but these mechanisms are inefficient at allowing a surgeon to definitively confirm a desired drilling depth has been reached. This is especially true for drilling that is conducted in connection with MIS procedures where visibility is low and in connection with the drilling of harder bone.

Therefore, there exists a need for improved surgical instruments and methods to overcome these deficiencies, including improved drill/depth guides.

BRIEF SUMMARY OF THE INVENTION

A first aspect of the invention includes a surgical instrument comprising a first housing having an internal bore and a first surface. The surgical instrument also has a shaft disposed within the internal bore, the shaft having a second surface that is matable with the first surface in a mating orientation, wherein upon rotation of the first surface relative to the second surface in the mating orientation, a tactile and/or auditory signal is provided.

In embodiments of the first aspect, the surgical instrument is a drill guide and the shaft is a drill bit. The shaft of the drill bit may include a flange, the second surface being disposed on the flange and facing a direction towards a distal end of the shaft. In addition, the first surface may include one of a recess or a protrusion, and the second surface may include the other of the recess or the protrusion.

A second aspect of the invention includes a method of using a surgical instrument comprising moving a first surface of the surgical instrument against a second surface of the surgical instrument to provide tactile, auditory, and/or visual feedback to a user that the surgical instrument is being utilized appropriately.

Embodiments of the second aspect include inserting a drill bit into a first housing of the surgical instrument so that a fluted end of the drill bit drills into bone. In addition, the first surface may include a plurality of recesses and the second surface may include one or more protrusions for engaging the recesses.

BRIEF DESCRIPTION OF THE DRAWINGS

A more complete appreciation of the subject matter of the present invention and of the various advantages thereof can be realized by reference to the following detailed description in which reference is made to the accompanying drawings in which.

DETAILED DESCRIPTION

In describing certain aspects of the present invention, specific terminology will be used for the sake of clarity. However, the invention is not intended to be limited to any specific terms used herein, and it is to be understood that each specific term includes all technical equivalents, which operate in a similar manner to accomplish a similar purpose.

Figure 1:
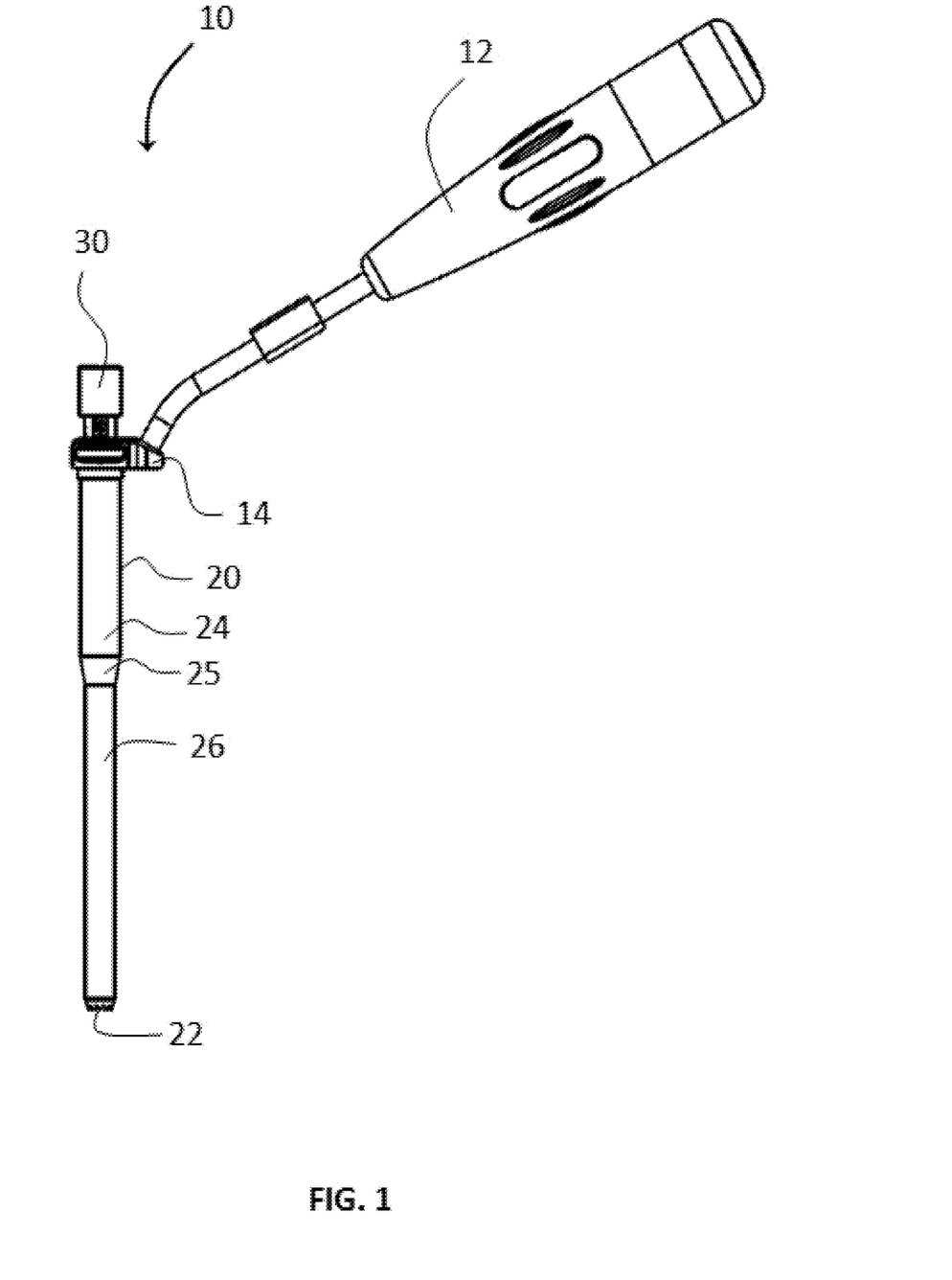
FIG. 1 is a side view of a drill guide according to an embodiment of the invention.

FIG. 1 is a side view of a drill guide 10 according to an embodiment of the present invention. As shown, drill guide 10 includes a handle 12, an outer tube or shaft 20, and an inner tube or shaft 30. A drill bit 50 (best shown in FIGS. 7A-C) is insertable into inner shaft 30. In use, inner shaft 30 is capable of being axially adjusted (e.g., moved into and out of) relative to outer shaft 20 to change the insertion-depth characteristics for drill guide 10. Drill bit 50 and inner shaft 30 also have tactile, auditory, and/or visual features thereon to allow a surgeon to easily determine when drill bit 50 has reached its maximum penetration depth. Such features are set forth in more detail below.

Figure 2:
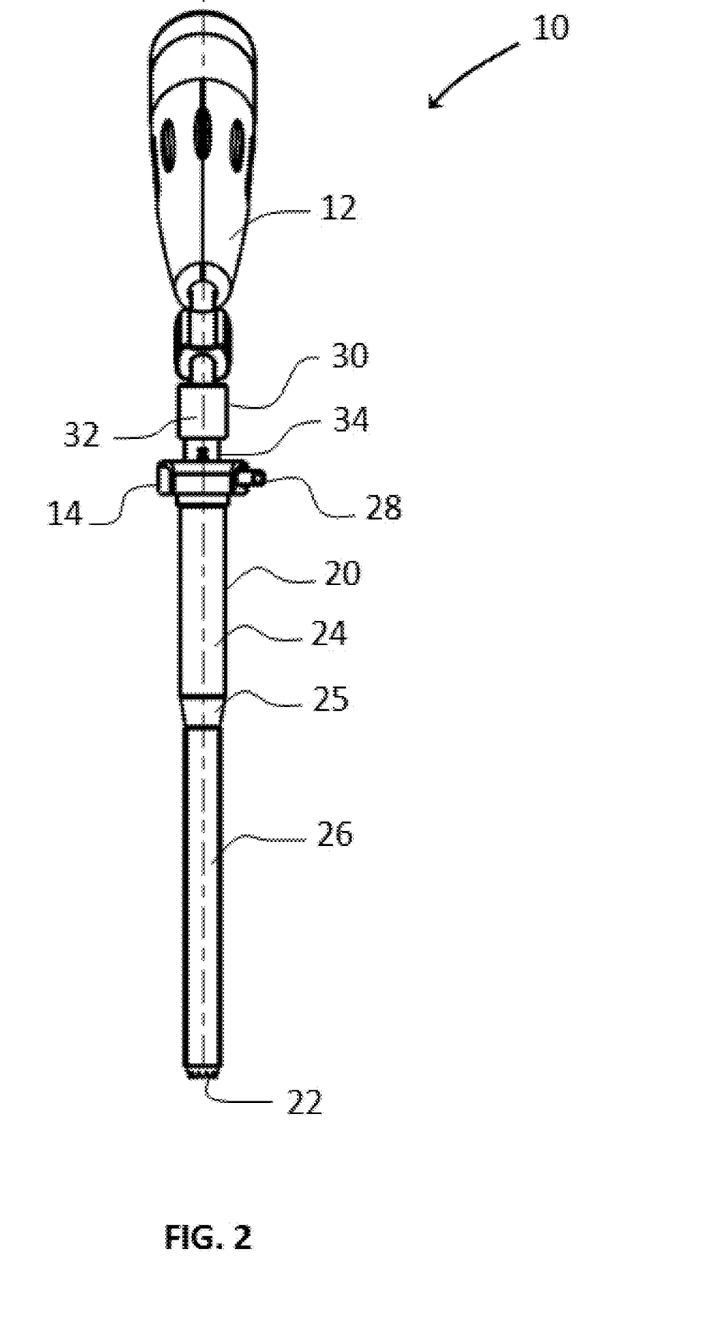
FIG. 2 is a front view of the drill guide of FIG. 1.
Figure 3:
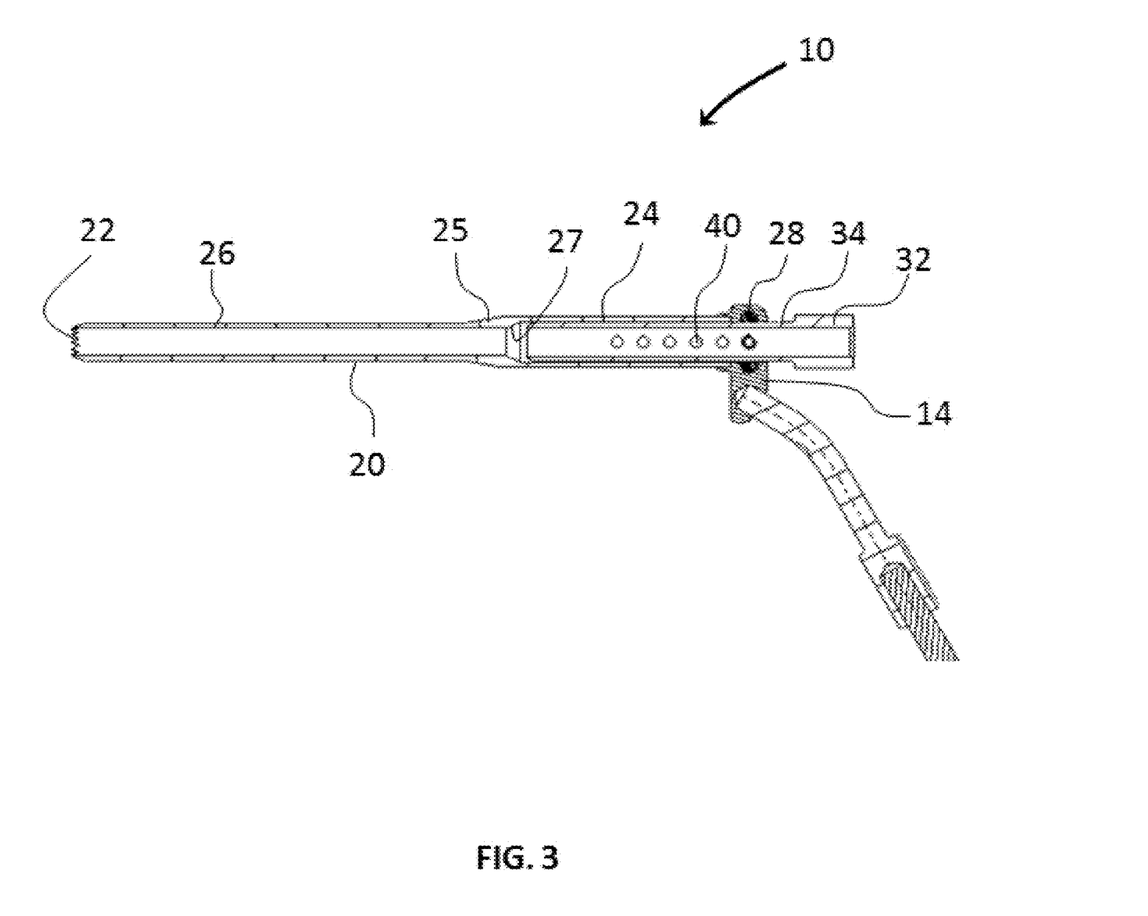
FIG. 3 is a cross-sectional view of the drill guide of FIG. 1.

As shown in FIGS. 2-3, outer shaft 20 of drill guide 10 has a larger diameter section 24, a smaller diameter section 26, and a tapered region 25 therebetween. Outer shaft 20 is cannulated or hollow along its length. Thus, outer shaft 20 is configured to receive inner shaft 30, as shown best in the cross-sectional view of FIG. 3. Likewise, inner shaft 30 includes a larger diameter head section 32 and a smaller diameter shaft section 34 that form a step therebetween. Shaft 34 fits within larger diameter section 24 of outer shaft 20 (e.g., shaft 34 has an outer diameter slightly smaller than the internal diameter of section 24 of outer shaft 20). However, shaft 34 has an outer diameter that is greater than an internal diameter of smaller diameter section 26 of outer shaft 20. Thus, in an embodiment, a distal end of shaft 34 cannot travel past the juncture between sections 24, 26 of outer shaft 20. As an example, the distal end of shaft 34 comes into contact with an internal tapered region 27 (FIG. 3) between sections 24, 26 of outer shaft 20 when shaft 34 is moved too far distally within outer shaft 20.

Inner shaft 30 also includes a plurality of openings 40 (FIG. 3) for locking inner shaft 30 relative to outer shaft 20, both rotationally and longitudinally, at different positions. A single opening could be provided to allow for locking at a single position. As shown in FIG. 2, body 14 of drill guide 10 includes a trigger or button 28 that, in an embodiment, includes a male feature (e.g., a post, as shown in FIG. 3) that is insertable into each opening 40 of inner shaft 30. In a particular embodiment, the post of button 28 is biased towards shaft section 34 of inner tube 30 (e.g., via a spring mechanism), and button 28 provides a mechanism for disengaging the post from a particular opening 40. In this manner, button 28 may be depressed to disengage the post of button 28 from a particular opening 40, and inner shaft/tube 30 may be moved axially within outer shaft/tube 20 until another desired opening 40 is reached, at which point the post may automatically spring into engagement with that opening 40 (i.e., due to the post being biased to move into such opening 40). A surgeon is therefore afforded an opportunity to easily adjust the position of inner shaft 30 relative to outer shaft 20 to control the insertion depth of drill bit 50, as described in more detail below.

In an embodiment, inner shaft 30 is also disposable and configured for one-time use. In this regard, it is contemplated to construct the various components of drill guide 10 and drill bit 50 of various materials. For instance, in one embodiment, outer shaft 20 and drill bit 50 are of a metallic construction, while inner shaft 30 is of a polymeric construction. This is particularly advantageous given that inner shaft 30 may be designed for single use and given the tactile and/or auditory features discussed below. The weaker polymeric material ensures that any damage caused by such features occurs to the single use component (e.g., inner shaft 30) and not drill bit 50 or any other component of the system designed for more than one use. Alternatively, in another embodiment, drill bit 50 is disposable and configured for one-time use. In this embodiment, inner shaft 30 and the remainder of drill guide 10 may be of a metallic construction, while portions or all of drill bit 50 are of a polymeric construction. In a particular embodiment, only flange 58 and the remainder of drill bit 50 extending to tool-engaging end 62 are composed of a polymeric material, and fluted part 52 and shaft 56 are of a metallic construction. Alternatively, only flange 58 may be composed of a polymeric material, while the remainder of drill bit 50 is of a metallic construction. As described in more detail below, this creates a situation in which only the polymeric parts of drill bit 50 are damaged during use and, since drill bit 50 is disposable and configured for one-time use, any drill bit 50 used during surgery may be easily disposed of and another fresh drill bit 50 used during the procedure, if needed.

Figure 4A:
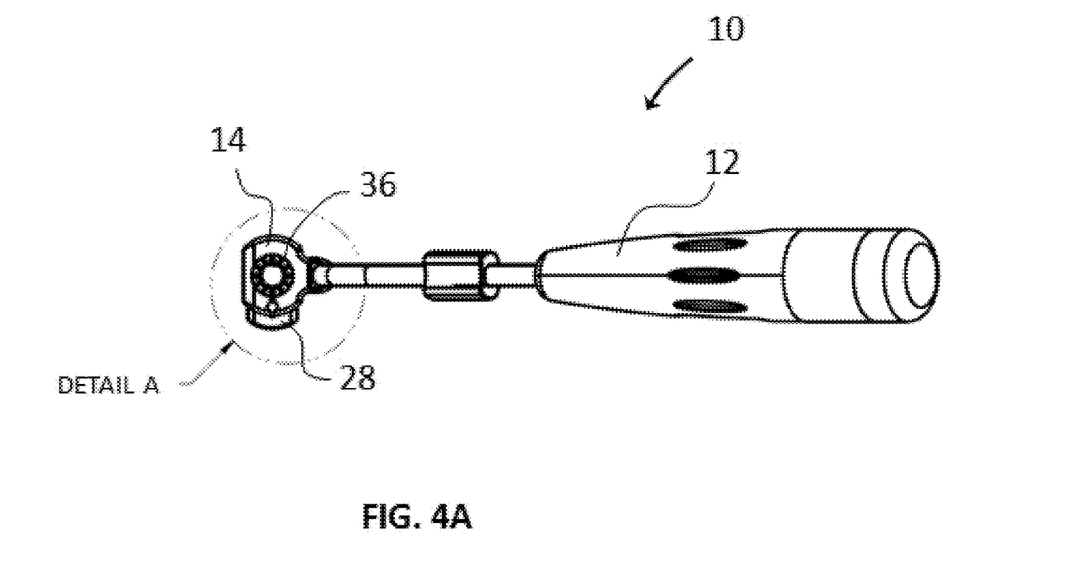
FIG. 4A is a top view of the drill guide of FIG. 1.
Figure 4B:
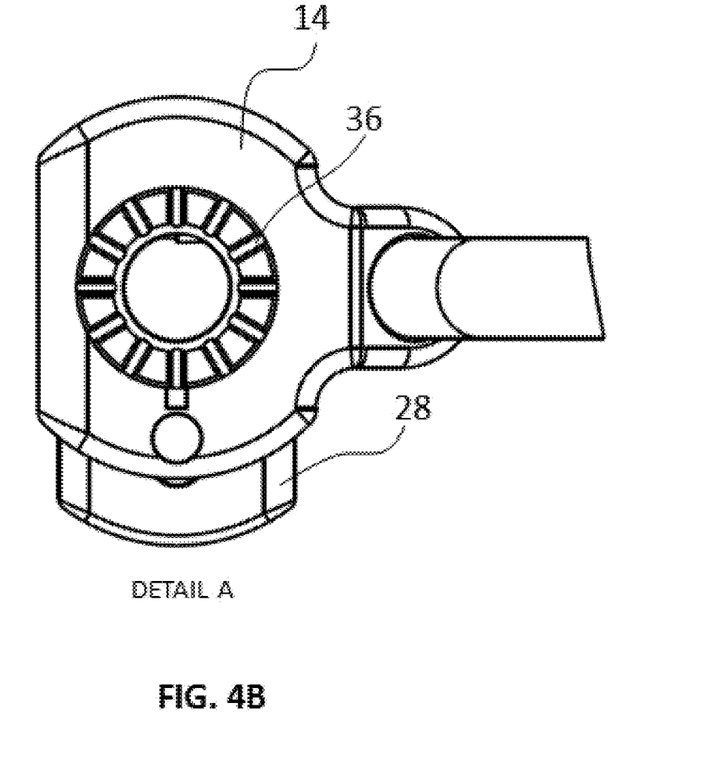
FIG. 4B is a close-up view of Detail A of FIG. 4A.
Figure 6:
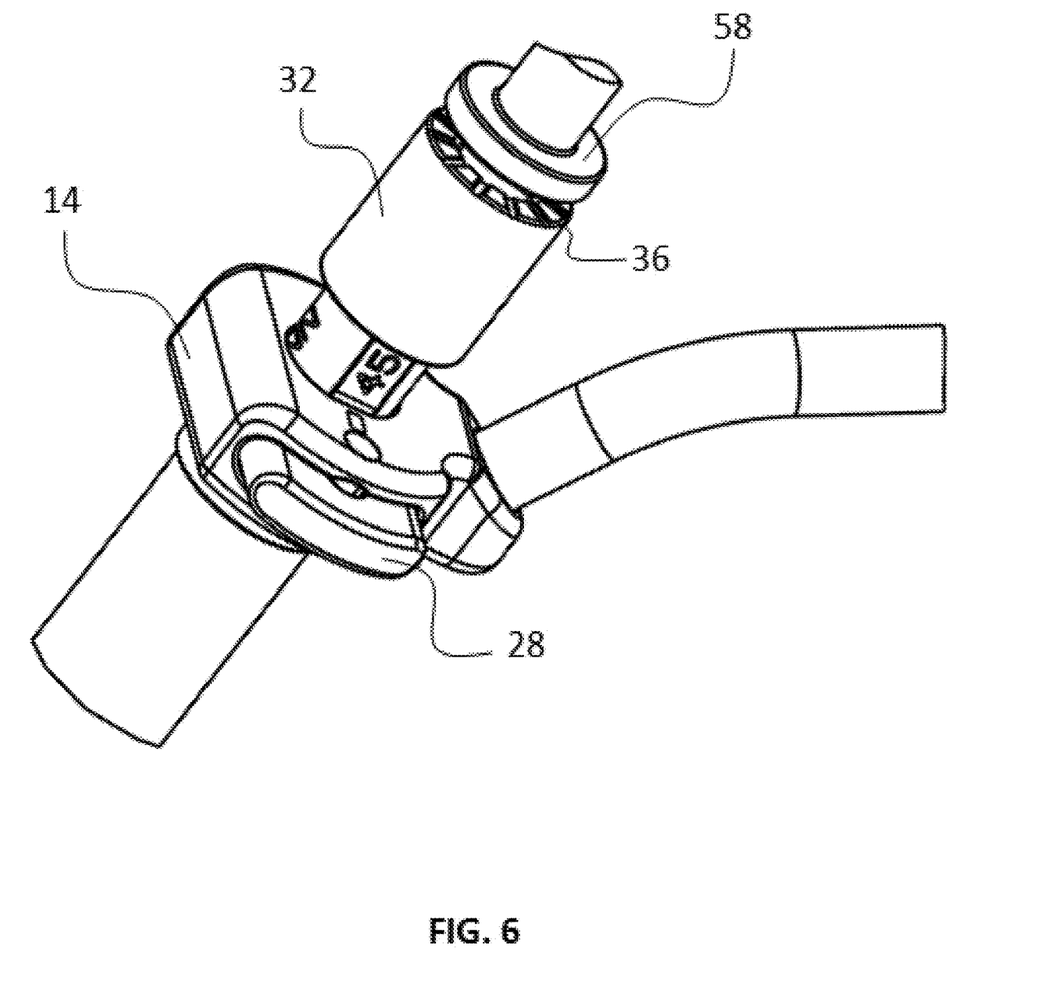
FIG. 6 is a close-up perspective view of part of the drill guide of FIG. 1, with a drill bit inserted therein.

As illustrated in FIGS. 4A-B and FIG. 6, a proximal end of inner shaft 30 includes a rumble strip 36. In an embodiment, rumble strip 36 comprises a series of indentations or recesses arranged circumferentially about the proximal end of inner shaft 30. Any number of indentations or recesses may be provided, although twelve (12) are shown in the figures. As an example, there may be between two (2) to twenty five (25) indentations or recesses. The recesses of rumble strip 36 may have a height ranging from 0.1 mm to 4 mm. In the depicted embodiment, twelve (12) recesses are provided on rumble strip 36, and adjacent recesses are separated by anywhere from about fifteen degrees (15°) to about forty five degrees (45°), most preferably about thirty degrees (30°). The recesses of rumble strip 36 are straight, in an embodiment, and arranged substantially perpendicular to the outer circumferential edge of head 32 of inner shaft 30 at the location of each recess. In other embodiments, the recesses of rumble strip 36 are curved or may form an S-shape. Stated differently, although each recess of rumble strip 36 is straight from a first end to a second end in the depicted embodiment, each recess may alternatively be curved or form an S-shape from its first end to its second end. In a further embodiment, the recesses of rumble strip 36 need not be separate recesses, and could be a single continuous recess or a series of substantially continuous recesses that form roughly a sine wave along the proximal end of inner shaft 30. Rumble strip 36 is arranged on a surface of inner shaft 30 that faces in a direction extending away from a distal end of drill guide 10, for example so that rumble strip 36 is designed to come into contact with a mating feature provided on a surface of drill bit 50 (described below) that faces in a direction extending towards the distal end of drill guide 10.

Shaft 34 of inner tube 30 also includes, in an embodiment, depth markings 38 so that a surgeon can accurately set the maximum drilling depth for drill guide 10. As an example, FIG. 6 shows that drill guide 10 is set for a maximum of 45 mm (4.5 cm) drilling depth. If button 28 was engaged and shaft 34 was moved more proximally, another depth marking 38 might reveal itself (e.g., a 35 mm marking) to indicate the new drilling depth to the surgeon. The post associated with button 28 could then snap into place in the relevant opening 40 to lock inner tube 30 rotationally and longitudinally relative to outer tube 20 and set the drilling depth for drill guide 10 to 35 mm. In the embodiment shown, moving shaft 34 proximally decreases maximum drilling depth, while moving shaft distally increases maximum drilling depth. Shaft 34 of inner tube 30 may include depth markings 38 that range from 45 mm to 20 mm in 5 mm increments, although other ranges are possible.

Figure 5A:
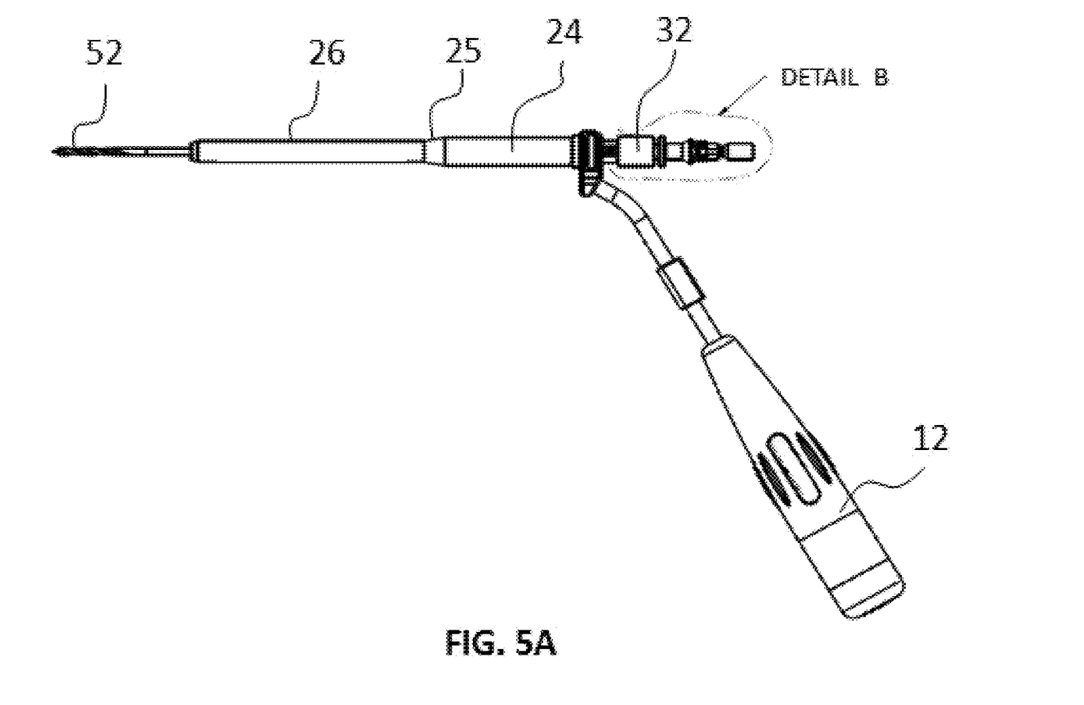
FIG. 5A is a side view of the drill guide of FIG. 1 with a drill bit inserted therein.
Figure 5B:
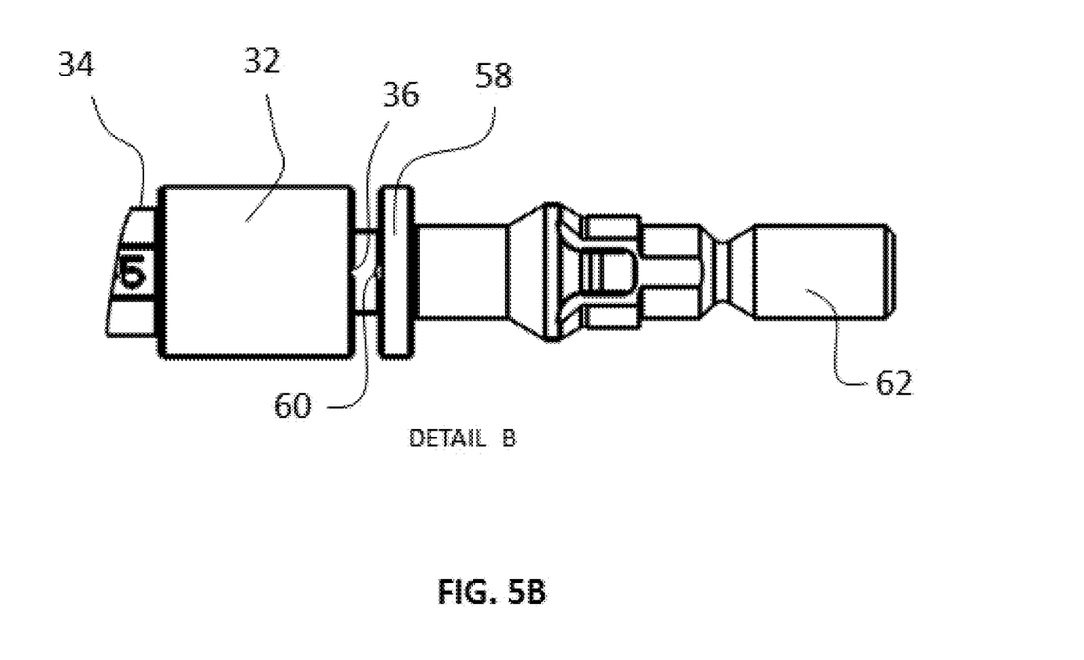
FIG. 5B is a close-up view of Detail B of FIG. 5A.
Figure 7A:
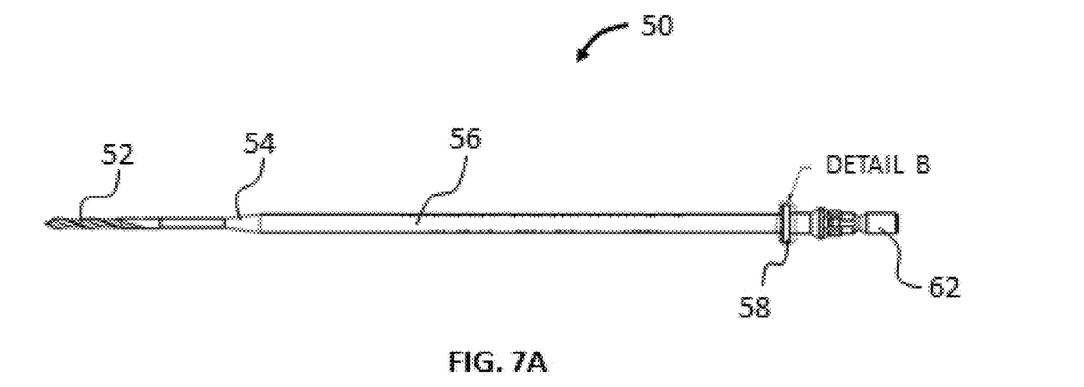
FIG. 7A is a side view of an embodiment of a drill bit that is usable with the drill guide of FIG. 1.
Figure 7B:
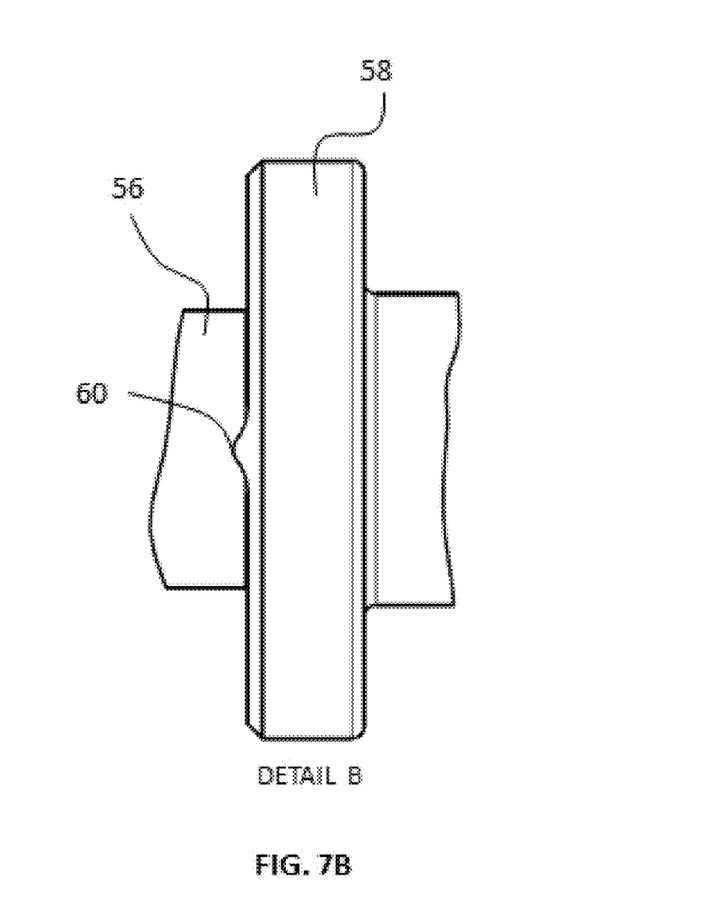
FIG. 7B is a close-up view of Detail B of FIG. 7A.
Figure 7C:
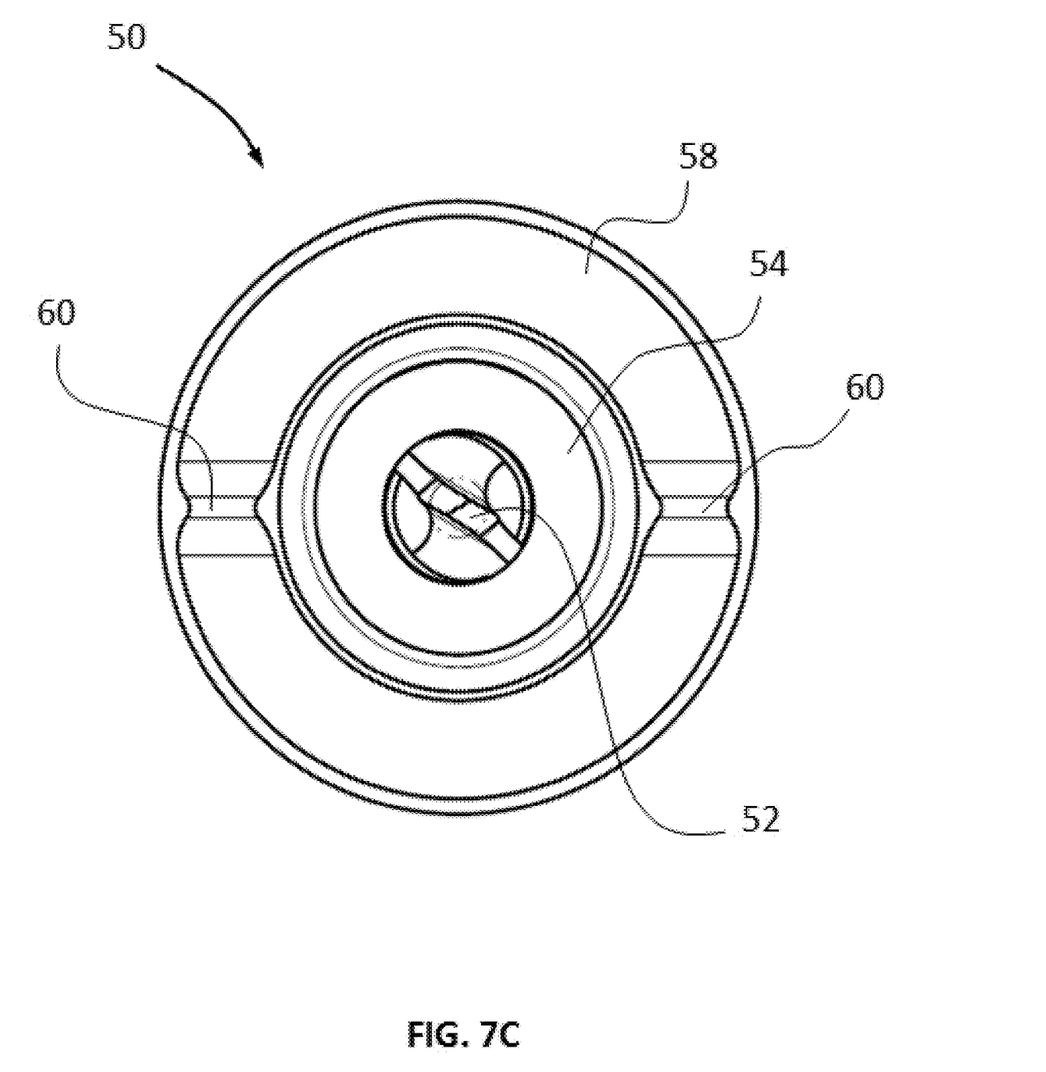
FIG. 7C is a front view of the drill bit of FIG. 7A.

FIGS. 7A-C show an embodiment of a drill bit 50 that is usable with drill guide 10, and FIGS. 5A-B show drill bit 50 inserted within drill guide 10. Drill bit 50 has a distal end with a fluted section 52 (e.g., for drilling into bone), a tapered section 54, and a shaft 56 with a diameter larger than fluted section 52 extending proximal of tapered section 54. A flange 58 is also provided on drill bit 50 for controlling the insertion depth of drill bit 50. When flange 58 comes into contact with a portion of inner tube 30, drill bit 50 is prevented from further distal movement and drilling. It is noted that drill bit 50 is but one drill bit useable with drill guide 10, and other embodiments may vary in their construction. For instance, other suitable drill bits may not be fluted and may include longer or shorter cutting sections.

Flange 58 includes a surface facing in a direction towards fluted section 52, the surface having a mating feature 60 thereon for interacting with rumble strip 36 of inner tube 30. Although it is envisioned to include a single protrusion, in the depicted embodiment, mating feature 60 includes a plurality of protrusions that extend outwards from flange 58 for mating with the recesses provided on rumble strip 36. The protrusions of mating feature 60 may have a height ranging from 0.1 mm to 4 mm. In an embodiment, the protrusions of mating feature 60 may have a height that is the same or different than the height of the recesses of rumble strip 36, within the specified ranges. Of course, it is equally possible that flange 58 may include the female feature (i.e., a recess or recesses), while inner tube 30 may include the male feature (i.e., a protrusion or protrusions). In the depicted embodiment, the number of protrusions of mating feature 60 (e.g., two (2)) is different than the number of recesses of rumble strip 36 (e.g., twelve (12)), although it is equally contemplated that, in an alternate embodiment, the number of protrusions and recesses are equal. The number of protrusions of mating feature 60 may be anywhere from two (2) to twelve (12) protrusions.

Additionally, other male/female features may be used to provide tactile and/or auditory feedback to a surgeon during use. For example: (i) roughened mating surfaces may be used on flange 58 and inner tube 30, (ii) contact between dissimilar surfaces on flange 58 and inner tube 30 that produces a vibration and/or auditory effect, (iii) a hard stop mechanism may be provided on inner tube 30 to prevent further rotation of drill bit 50 relative thereto when drill bit 50 reaches its maximum depth, or (iv) an electronic switch can be provided on drill bit 50 and/or drill guide 10 that, when triggered at drill bit 50's maximum insertion depth, emits a sound, light, or causes vibration to indicate to the surgeon that drill bit 50 has reached its maximum depth. As to the "hard stop" embodiment, it is contemplated that flange 58 and shaft 34 may, in an embodiment, include mating protrusions that contact each other to prevent further rotation of drill bit 50 when it reaches its maximum depth. Any combination of the foregoing features could also be utilized (e.g., a rumble strip in addition to an electronic switch mechanism).

In the depicted embodiment, the protrusions of mating feature 60 of flange 58 (FIG. 7C) come into contact with the recesses of rumble strip 36 when drill bit 50 reaches its maximum depth (approaching maximum depth in FIG. 6), causing flange 58 to engage the proximal end or head 32 of inner tube 30. Further rotation of drill bit 50 causes the protrusions of mating feature 60 to successively engage the recesses of rumble strip 36 and create a "rumbling" feeling and/or sound through drill bit 50. In this way, the surgeon will feel a vibration through drill bit 50 and/or hear a sound when drill bit 50 reaches its maximum depth. This tactile and/or auditory feedback provided to the surgeon becomes important in instances where it is difficult for the surgeon to tell when drill bit 50 has reached its maximum depth. As an example, when drilling into predominantly cortical bone, which is hard bone making for difficult drilling, the surgeon might not realize that drill bit 50 has failed to reach its maximum depth because the significant hardness of the bone may make the surgeon prematurely believe that flange 58 has contacted the proximal end of inner tube 30. In other instances, the surgeon might believe that further drilling is required even though drill bit 50 is incapable of further distal movement (e.g., because cortical bone presents a hard surface that would feel similar to flange 58 engaging the proximal end of inner tube 30). Thus, the mating features discussed above provide the surgeon with tactile and/or auditory feedback to confirm that the final drilling depth of drill bit 50 has been reached. This confirms to the surgeon that no further drilling is needed. If inner tube 30 is constructed of a polymer or otherwise weaker material than drill bit 50, or alternatively if parts of drill bit 50 are of a polymeric construction, as described above, it is ensured that any damage that occurs during engagement of rumble strip 36 and mating feature 60 occurs to inner tube 30 or drill bit 50, as the case may be, which in some embodiments are designed as single-use components. The single-use component (drill bit 50 or inner tube 30) can be discarded and another single-use component used for drilling another hole during the procedure. In this way, accurate use of the rumble strip 36 and mating feature 60 are ensured when drilling multiple holes in a surgical procedure, as the single-use component is disposed of after drilling each hole and a new single-use component is provided with a fresh rumble strip 36 or mating feature 60.

In use, drill guide 10 is first assembled by way of selecting a particular inner shaft/tube 30 for use with guide 10, and then inserting inner tube 30 into outer tube 20. Button 28 may be depressed during and/or after insertion to calibrate the position of inner tube 30 relative to outer tube 20. In this regard, depressing button 28 causes the post thereof to move out of the way of inner tube 30 (e.g., during initial insertion into outer tube 20), or to simply move out of engagement with a particular opening 40. Then, inner tube 30 may be slid relative to outer tube 20 until a particular depth marking 38 is reached, at which point the post of button 28 may spring into place in the relevant opening 40, causing inner tube 30 to be locked rotationally and longitudinally relative to outer tube 20. Drill guide 10 is then ready for use, and a surgeon may grasp handle 12 and place guide 10 against the bone (e.g., vertebral body) to be drilled. Teeth 22 on drill guide 10 may be used to secure guide 10 to the bone.

Then, drill bit 50 may be inserted into inner tube 30 and moved distally for drilling the bone. In an embodiment, a drill bit 50 corresponding to the size of the bone screw being used in the surgical procedure may be selected. For instance, if a 3.5 mm diameter bone screw is being used in the surgical procedure, a drill bit 50 having a fluted section 52 that is 2.5 mm to 3 mm in diameter might be selected for the procedure. A number of drill bits 50 with different diameter fluted sections 52 may be provided with drill guide 10 to satisfy the particular needs of the patient and surgical procedure at hand, as can differently sized inner tubes 30. The selected drill bit 50 can then be inserted into the selected inner tube 30 so that its larger diameter shaft 56 closely conforms to the inner diameter of shaft 34 of inner tube 30, and fluted section 52 extends into smaller diameter section 26 of outer tube 20. In this regard, each of the different drill bits 50 with different diameter fluted sections 52 may all have roughly the same or the same exact diameter shaft 56 so that each drill bit 50 glides smoothly within shaft 34 of inner tube 30. In other words, the outer diameter of shaft 56 of each drill bit 50 may be only slightly less than the internal diameter of shaft 34 of inner tube 30 so that each drill bit's shaft 56 glides smoothly within shaft 34 of inner tube 30. This allows, for example, many differently sized drill bit 50's (i.e., in terms of the diameter of their fluted sections 52) to be used with drill guide 10. As an example, up to or more than five (5) drill bit's 50 with different diameter fluted sections 52 can be accommodated with drill guide 10. Of course, in other embodiments, differently sized and/or configured inner tubes 30 could be provided to be utilized with correspondingly sized and configured drill bits 50.

The selected drill bit 50 is then driven by the surgeon distally through drill guide 10 and into bone. Drill bits 50 may include a tool engaging end 62 (FIG. 7A) for this purpose, which in an embodiment include a recess for mating with a driver. The recess may be any shape known in the art, including square, hexagonal, diamond shaped, etc. for engaging with a driver having a male driving end with a complementary shape. Of course, drill bit 50 may include a male engaging end for engagement with a female tool. In addition, it is contemplated that tool-engaging end 62 may be configured for attachment to a powered drill.

As the selected drill bit 50 approaches its maximum drilling depth (FIG. 6), flange 58 approaches the proximal end of inner tube 30 and ultimately comes into contact with the same. At this point, the protrusions of mating feature 60 of flange 58 successively engage the recesses of rumble strip 36 due to further rotation of drill bit 50, which causes a tactile (e.g., vibration) and/or auditory signal to be sent to the surgeon. The surgeon then knows that the maximum drilling depth for drill bit 50 has been reached, and ceases drilling. An appropriate screw selected for the procedure can then be inserted into the drilled hole. As an example, drill guide 10 can be used in any number of spinal stabilization and/or fixation procedures. For instance, the screw could be used for attachment of a spinal rod to the spine (e.g., in the case of a pedicle screw having a coupling element or tulip), for attachment of a standalone vertebral cage or plate, or for any other spinal procedure necessitating the use of screws. If other bone-screw holes are needed for the procedure, and a single-use component (drill bit 50 or inner tube 30) is used, the single-use component can be disposed of after drilling the initial bone-screw hole. A second single-use component (drill bit 50 or inner tube 30) can then be selected and used for drilling a subsequent bone-screw hole in the manner described above. As is appreciated, this process can repeat itself depending upon the number of bone-screw holes required for the procedure.

Figure 8A:
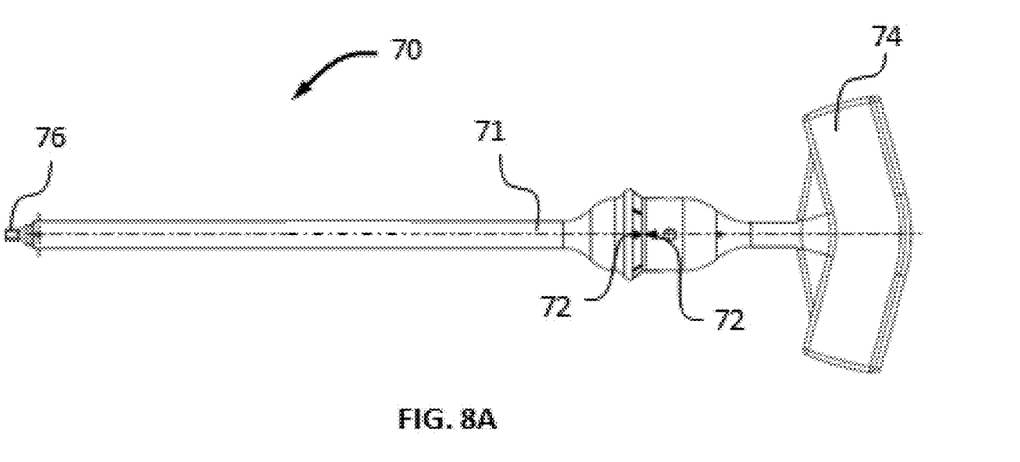
FIG. 8A is a side view of a torque wrench according to an embodiment of the invention.
Figure 8B:
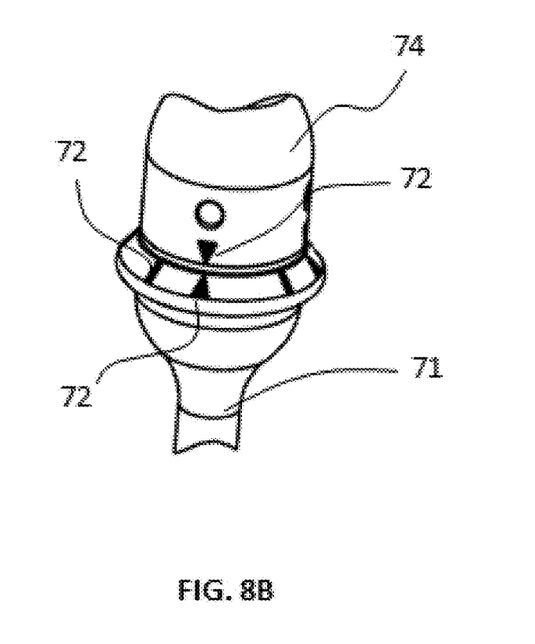
FIG. 8B is a close-up view of part of the torque wrench of FIG. 8A.

Additional instrumentation may also use any of the features discussed above to provide a surgeon with tactile and/or auditory feedback. As an example, FIGS. 8A-B illustrate a torque wrench 70 that may be modified to include any of the above-mentioned tactile and/or auditory features. Torque wrench 70 has visual indicators 72, a body 71, and a T-handle 74 having a shaft. Body 71 is cannulated, in an embodiment, and is thereby adapted to receive T-handle 74 and its shaft so that a driving end 76 thereof protrudes from body 71, as shown in FIG. 8A. Rotation of T-handle 74 and its shaft within body 71 causes driving end 76 to rotate and drive, as an example, a set screw. In addition, rotation of T-handle 74 relative to body 71 is constrained by a torsion bar (not shown) or other like structure within body 71. The torsion bar is configured to assist with ensuring T-handle 74 is rotated at a specific set force (e.g., 8 Nm).

Further, visual indicators 72 are provided so that, when T-handle 74 is rotated clockwise relative to body 71, certain visual indicators 72 align to indicate to a surgeon that T-handle 74 has reached its maximum force output. Stated another way, T-handle 74 is rotated clockwise in FIGS. 8A-B, causing visual indicator 72 on T-handle 74 to move to the left in FIG. 8B and align with the left-most visual indicator 72 in FIG. 8B. At that stage, a surgeon is afforded visual confirmation that the maximum torque or output force for T-handle 74 has been reached. However, no tactile and/or auditory feedback is given to the surgeon and it is often difficult to use visual indicators 72. Thus, an embodiment of the present invention contemplates using any of the above-mentioned tactile and/or auditory features with torque wrench 70 to provide for a better indication that T-handle 74 has reached its maximum output. As an example, any of the above-mentioned tactile and/or auditory features (e.g., a rumble strip and mating male feature) may be placed at the interface between T-handle 74 and body 71, as shown in FIG. 8B. In other words, the surface on T-handle 74 that faces and mates with the corresponding surface on body 71, as shown in FIG. 8B, can have any of the above-mentioned tactile and/or auditory features. Thus, upon rotation of T-handle 74 to its maximum torque position, a surgeon can be afforded tactile and/or auditory feedback, in addition to visual feedback via indicators 72 as described above, to confirm that T-handle has reached its maximum torque position.

Figure 9A:
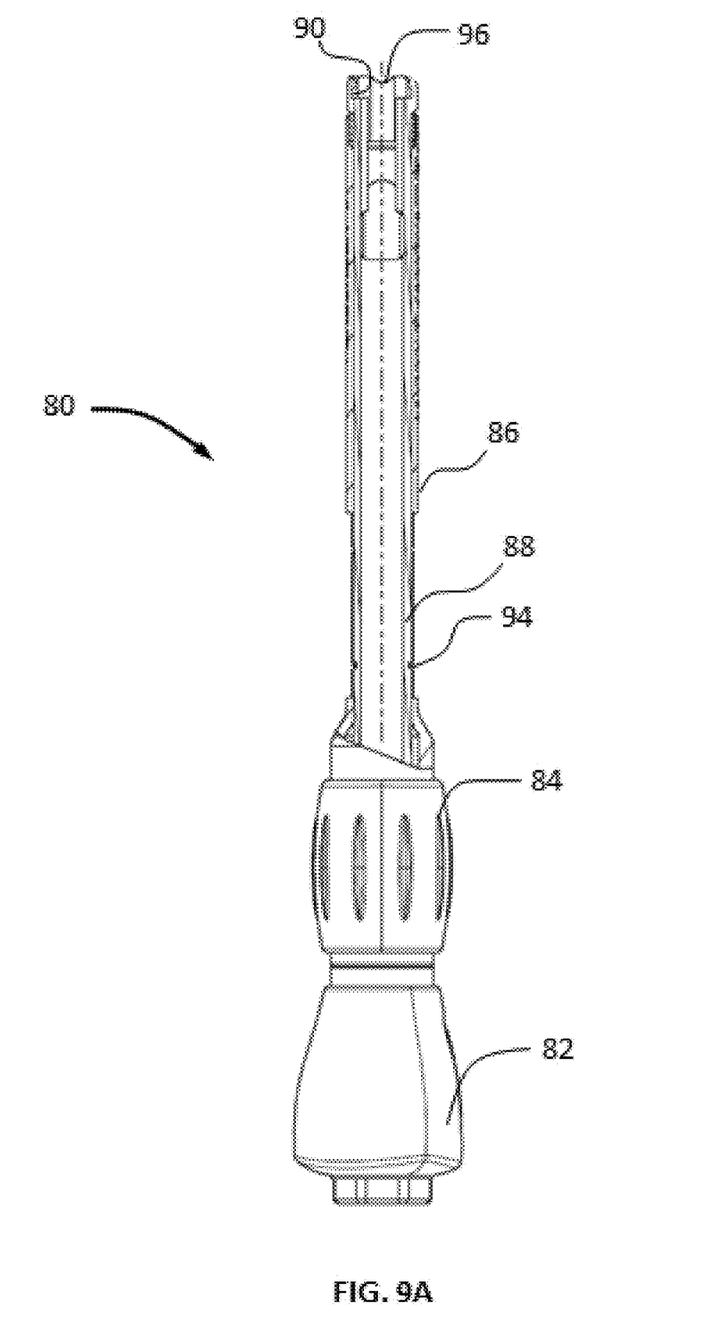
FIG. 9A is a cross-sectional view of a rod persuader according to an embodiment of the invention.
Figure 9B:
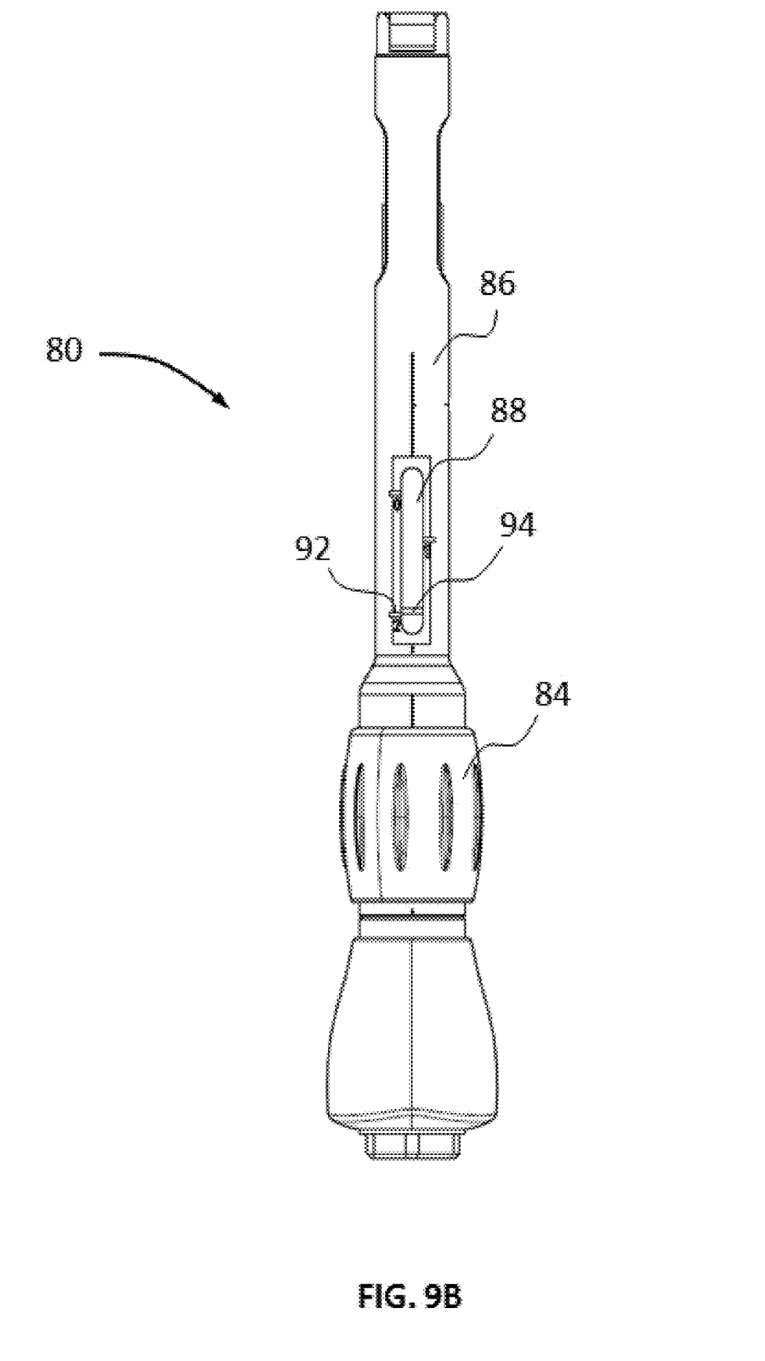
FIG. 9B is a side view of the rod persuader of FIG. 9A.

Yet another instrument is shown in FIGS. 9A-B. A rod persuader 80 is illustrated, and it includes a rotatable knob 82 and a stationary knob 84. Stationary knob 84 is engaged with a stationary shaft 86, while rotatable knob 82 is engaged with a movable shaft 88 disposed within stationary shaft 86. In an embodiment, rotatable knob 82 has an internally-threaded portion that engages with an externally-threaded portion of movable shaft 88 so that, when rotatable knob 82 is rotated, movable shaft 88 moves in a distal or proximal direction depending upon the direction of rotation of knob 82. As an example, clockwise rotation of knob 82 causes distal movement of movable shaft 88, while counterclockwise rotation of knob 82 causes proximal movement of movable shaft 88.

A distal end of persuader 80 has geometric features 90 (e.g., a circumferential recess), as shown in FIG. 9A, for engaging a tulip part of a pedicle screw. In addition, persuader 80 has one or more visual indicators 92 thereon (e.g., numbers "0", "1", and "2") that indicate certain conditions of persuader 80. Likewise, movable shaft 88 has a visual indicator 94 in the form of, for instance, a circumferential groove or laser line, that is designed to align with each visual indicator 92 of persuader 80. Thus, as an example, when visual indicator 94 of movable shaft 88 is aligned with the "2" visual indicator 92 of persuader 80, persuader 80 is in a position in which geometric features 90 of persuader 80 can engage the tulip portion of the pedicle screw. Upon rotation of knob 82 and movement of movable shaft 88 in a distal direction, visual indicator 94 thereof comes into alignment with the "1" visual indicator 92 of persuader 80, thereby causing geometric features 90 to engage and lock to the tulip part of the pedicle screw. In this condition, persuader 80 is arranged to "persuade" or drive a spinal rod to be fully seated in the tulip part of the pedicle screw. Persuader 80 has a semicircular cutout 96 in a distal end of movable shaft 88 for contacting rod and driving it into full engagement in the tulip part of the pedicle screw. Further rotation of knob 82 causes movable shaft 88 to move in a distal direction, with rod in cutout 96, thereby causing rod to be fully seated within the tulip part of the pedicle screw. This is reflected by visual indicator 94 of movable shaft 88 coming into alignment with the "0" visual indicator 92 of persuader 80.

Yet again, it is clear that visual indication is not particularly reliable on its own for the surgeon. Thus, an embodiment of the present invention contemplates using any of the above-mentioned tactile and/or auditory features, in addition to the visual features for persuader 80 set forth above, to provide further confirmation to the surgeon that the rod has been fully seated in the tulip part of the pedicle screw. As an example, movable shaft 88 may have on its external surface any of the tactile and/or auditory features noted above (e.g., a rumble strip), and stationary shaft 86 may have on its internal surface any of the tactile and/or auditory features set forth above (e.g., a set of protrusions for engaging with the rumble strip). When movable shaft 88 is finally moved to its "0" position, such tactile and/or auditory features may be actuated to provide the surgeon with firm conviction that the rod has been fully seated in the tulip part of the pedicle screw. For instance, the tactile and/or auditory features (e.g., rumble strip) on movable shaft 88 may only be on a portion of shaft 88's external surface, and the tactile and/or auditory features (e.g., protrusions) on stationary shaft 86 may only be on a portion of shaft 86's internal surface. Only upon reaching position "0" may these tactile and/or auditory features engage or be actuated to provide the surgeon with tactile and/or auditory confirmation that the desired point has been reached for movable shaft 88 and the rod.

As is clear from the embodiments above, the tactile and/or auditory features contemplated by embodiments of the present invention can have multiple uses in the context of different surgical instruments, with or without the addition of the visual features discussed above. Such tactile and/or auditory features either supplant or augment the visual features and provide the surgeon with greater confidence that the relevant instrument is being used appropriately.

Although aspects of the invention herein have been described with reference to particular embodiments, it is to be understood that these embodiments are merely illustrative of certain features of the present invention. It is therefore to be understood that numerous modifications may be made to the illustrative embodiments and that other arrangements may be devised without departing from the spirit and scope of the present invention as defined by the appended claims. For instance, the features described in connection with individual embodiments may be shared with others of the described embodiments.

It will also be appreciated that the various dependent claims and the features set forth therein can be combined in different ways than presented in the initial claims. In particular, each feature from the dependent claims may be shared with other features of other claims, to the extent technologically feasible, as if the claims were written in multiple dependent format.

The invention claimed is:

1. A surgical instrument comprising:
   a first housing having an internal bore and a first surface, the first surface located at a proximal end of the first housing and having a series of indentations arranged circumferentially around the first housing; and
   a shaft disposed within the internal bore, the shaft having a second surface that is matable with the first surface in a mating orientation, wherein upon rotation of the first surface relative to the second surface in the mating orientation, the series of indentations provide a tactile and/or auditory signal, wherein the first housing is made of a first material and the shaft is made of a second material, the first material being weaker than the second material such that the first surface is configured to be damaged prior to the second surface during rotation of the first surface relative to the second surface in the mating orientation.

2. A surgical instrument as claimed in claim 1, wherein the surgical instrument is a drill guide and the shaft is a drill bit.

3. A surgical instrument as claimed in claim 2, wherein the shaft of the drill bit includes a flange, the second surface being disposed on the flange and facing a direction towards a distal end of the shaft.

4. A surgical instrument as claimed in claim 3, wherein the second surface includes a recess or protrusion to mate with the series of indentations.

5. A surgical instrument as claimed in claim 4, wherein the indentations are a plurality of recesses and the second surface includes a plurality of protrusions.

6. A surgical instrument as claimed in claim 2, wherein the drill guide includes a drill guide body that has a second housing, and the first housing is insertable into the second housing.

7. A surgical instrument as claimed in claim 6, wherein the first housing is movable relative to the second housing from a first position to a second position, the first and second positions both being positions in which the first housing is locked longitudinally and rotationally relative to the second housing.

8. A surgical instrument as claimed in claim 7, wherein the first housing includes a set of openings and the second housing includes a button with a post that is selectively engageable with the openings to permit the first housing to move relative to the second housing from the first position to the second position.

9. A system including surgical instrument as claimed in claim 6, further comprising a plurality of drill bits each having a fluted part with different external diameters, wherein each of the drill bits is insertable into the first and second housings for drilling bone.

* * * * *